United States Patent
Miyaji (10) Patent No.: US 11,013,903 B2
(45) Date of Patent: May 25, 2021

(54) CLAMPING DEVICE

(71) Applicant: Nikkiso Company Limited, Tokyo (JP)

(72) Inventor: Hiroshi Miyaji, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 205 days.

(21) Appl. No.: 16/011,003

(22) Filed: Jun. 18, 2018

(65) Prior Publication Data

US 2018/0369565 A1    Dec. 27, 2018

Related U.S. Application Data (63) Continuation of application No. PCT/JP2016/088477, filed on Dec. 22, 2016.

(30) Foreign Application Priority Data

Dec. 22, 2015    (JP) .............................. JP2015-249889

(51) Int. Cl.
*A61M 39/28*    (2006.01)
*A61M 5/168*    (2006.01)
(Continued)

(52) U.S. Cl.
CPC ........ *A61M 39/284* (2013.01); *A61M 1/3626* (2013.01); *A61M 5/168* (2013.01); *A61M 5/16813* (2013.01); *A61M 5/44* (2013.01); *A61M 39/28* (2013.01); *A61M 39/281* (2013.01); *A61M 1/1601* (2014.02);
(Continued)

(58) Field of Classification Search
CPC ................ A61M 39/281; A61M 39/28; A61M 5/16813; A61M 1/3626; A61M 5/44; A61M 5/36; A61M 2205/3368; A61M 2205/3673; A61M 2205/3653; A61F 7/0085
See application file for complete search history.

(56) References Cited

U.S. PATENT DOCUMENTS

| | | |
|---|---|---|
| 350,850 A | 10/1886 | Tatum |
| 3,419,245 A | 12/1968 | Scola |

(Continued)

FOREIGN PATENT DOCUMENTS

| | | |
|---|---|---|
| CN | 2239266 Y | 11/1996 |
| CN | 202143737 U | 2/2012 |

(Continued)

OTHER PUBLICATIONS

International Search Report from the Japanese Patent Office for Application No. PCT/JP2016/088477 dated Feb. 21, 2017.
(Continued)

*Primary Examiner* — Nathan R Price
*Assistant Examiner* — Anne E Goldberg-Richmeier
(74) *Attorney, Agent, or Firm* — Young Basile Hanlon & MacFarlane, P.C.

(57) ABSTRACT

A clamping device that is always capable of clamping a flexible tube in a good manner and assuredly closing the flexible tube without a large clamping force. A clamping device includes a holding member that holds a flexible tube in which a fluid is allowed to flow, and a clamping member that clamps and closes a clamping portion of the flexible tube that is held by the holding member. The clamping device further includes a heating device that heats the clamping portion of the flexible tube.

17 Claims, 6 Drawing Sheets

(51) Int. Cl.
  *A61M 5/44* (2006.01)
  *A61M 1/36* (2006.01)
  *A61M 1/16* (2006.01)

(52) U.S. Cl.
  CPC .......... *A61M 1/367* (2013.01); *A61M 2205/14* (2013.01); *A61M 2205/3334* (2013.01)

(56) References Cited

U.S. PATENT DOCUMENTS

| | | |
|---|---|---|
| 3,698,681 A | 10/1972 | Lacey |
| 3,822,052 A | 7/1974 | Lange |
| 4,053,135 A | 10/1977 | Saliaris |
| 4,235,412 A | 11/1980 | Roth et al. |
| 4,589,626 A | 5/1986 | Kurtz et al. |
| 4,643,389 A | 2/1987 | Elson et al. |
| 5,203,056 A | 4/1993 | Funk et al. |
| 5,238,218 A | 8/1993 | Mackal |
| 5,827,238 A | 10/1998 | Kelley |
| 6,359,894 B1 | 3/2002 | Hong et al. |
| 6,592,558 B2 | 7/2003 | Quah |
| 6,789,118 B1 | 9/2004 | Rao |
| 7,516,211 B1 | 4/2009 | Gourlay et al. |
| 7,898,986 B2 | 3/2011 | Ford et al. |
| 8,325,630 B2 | 12/2012 | Khan et al. |
| 8,474,784 B2 | 7/2013 | Kashmirian et al. |
| 8,559,335 B2 | 10/2013 | Berman |
| 9,192,708 B2 | 11/2015 | Iwahori et al. |
| 9,211,381 B2 * | 12/2015 | Faries ...................... A61M 5/44 |
| 9,616,170 B2 * | 4/2017 | Nakanishi ......... A61M 5/14228 |
| 2002/0097687 A1 | 7/2002 | Meiri et al. |
| 2004/0089828 A1 | 5/2004 | Werth |
| 2005/0256447 A1 | 11/2005 | Richardson et al. |
| 2006/0048142 A1 | 3/2006 | Roese et al. |
| 2007/0189288 A1 | 8/2007 | Andrews et al. |
| 2007/0261214 A1 | 11/2007 | Nerbonne et al. |
| 2008/0053530 A1 | 3/2008 | Knight et al. |
| 2010/0152681 A1 | 6/2010 | Mathias |
| 2010/0268161 A1 | 10/2010 | Traversaz |
| 2011/0092893 A1 | 4/2011 | Demers et al. |
| 2012/0232497 A1 | 9/2012 | Singh |
| 2013/0166708 A1 | 6/2013 | Schlichter et al. |
| 2013/0310768 A1 | 11/2013 | Ebara et al. |
| 2013/0343379 A1 | 12/2013 | Stroud et al. |
| 2013/0343387 A1 | 12/2013 | Stroud et al. |
| 2014/0019607 A1 | 1/2014 | Beste et al. |
| 2014/0074047 A1 | 3/2014 | Calderon et al. |
| 2014/0336613 A1 | 11/2014 | Roth et al. |
| 2016/0158437 A1 * | 6/2016 | Biasi ................... F04B 43/0072 604/500 |
| 2016/0175552 A1 * | 6/2016 | Harrington ....... A61M 16/1045 128/201.13 |
| 2016/0361484 A1 * | 12/2016 | Utsugida ............... A61M 1/367 |
| 2017/0120038 A1 | 5/2017 | Tsukamoto et al. |
| 2017/0326294 A1 | 11/2017 | Kato et al. |
| 2018/0104467 A1 | 4/2018 | Kato et al. |
| 2018/0353324 A1 * | 12/2018 | Goldenberg ...... A61M 37/0076 |
| 2019/0388602 A1 * | 12/2019 | Ortega ..................... A61M 1/28 |

FOREIGN PATENT DOCUMENTS

| | | | |
|---|---|---|---|
| EP | 0637456 A1 | 2/1995 | |
| EP | 2332611 A1 | 6/2011 | |
| FR | 2379290 A1 * | 9/1978 | .......... A61M 39/281 |
| JP | S62-53667 A | 3/1987 | |
| JP | H03-73162 A | 3/1991 | |
| JP | H05-23792 B2 | 4/1993 | |
| JP | 2001-025505 A | 1/2001 | |
| JP | 2001-353215 A | 12/2001 | |
| JP | 2002-210006 A | 7/2002 | |
| JP | 2003-235971 A | 8/2003 | |
| JP | 2004-313522 A | 11/2004 | |
| JP | 2005-027721 A | 2/2005 | |
| JP | 2009-022744 A | 2/2009 | |
| JP | 2009-207706 A | 9/2009 | |
| JP | 2011-161000 A | 8/2011 | |
| JP | 2012-075520 | 4/2012 | |
| JP | 4922246 B2 | 4/2012 | |
| JP | 2013-176543 A | 9/2013 | |
| JP | 2013-245664 A | 12/2013 | |
| JP | 2014-530076 A | 11/2014 | |
| WO | 2012-111310 A1 | 8/2012 | |
| WO | 2014-162376 A1 | 9/2014 | |
| WO | 2015/118776 A1 | 8/2015 | |

OTHER PUBLICATIONS

Co-pending U.S. Appl. No. 15/392,748 published as US2017/0120038 filed on Dec. 28, 2016.

Co-pending, U.S. Appl. No. 15/664,635 published as US 2017/0326294 filed on Aug. 1, 2017.

Co-pending U.S. Appl. No. 15/844,764 published as US2018/0104467 filed on Dec. 18, 2017.

Extended European Search Report for Application No. 16878963.4 dated Jul. 17, 2019.

Chinese Office Action dated Mar. 23, 2020 from corresponding Chinese Application 201680075260.2.

* cited by examiner

CLAMPING DEVICE

FIELD

The present invention relates to a clamping device including a holding member that is capable of holding a flexible tube in which a fluid is allowed to flow, and a clamping member that is capable of closing, as intended, a predetermined part of the flexible tube, which is held by the holding member, by pressing the predetermined part.

BACKGROUND

There is a proposal of a blood glucose controlling device (see PTL 1, for example) in which while blood is collected from the body of a patient, the blood is diluted with a predetermined diluent and the blood sugar level of the blood is measured in real time with a blood-sugar-level-measurement device such as a glucose sensor. If the measured blood sugar level is too high, insulin is injected into the patient so that the blood sugar level can be lowered. If the measured blood sugar level is too low, grape sugar (glucose) is injected into the patient so that the blood sugar level can be raised.

Such a blood glucose controlling device includes an injection line formed of a flexible tube through which either the insulin or the glucose can be injected into the patient. Furthermore, the blood glucose controlling device is provided with a bubble-detecting device that is capable of detecting bubbles contained in the liquid flowing in the injection line, and a clamping device including a clamping member that is capable of clamping and closing the injection line if any bubbles are detected by the bubble-detecting device. Hence, if the liquid contains any bubbles in the process of injecting the insulin or the glucose into the patient, the injection line is closed and the bubbles can be prevented from reaching the body of the patient.

CITATION LIST

Patent Literature

PTL 1: Japanese Unexamined Patent Application Publication No. 2013-245664

SUMMARY

In the clamping device according to the above known technique, however, if the temperature of the clamping portion of the flexible tube is low, good clamping with the clamping member may be hampered. That is, if the temperature is low, the flexible tube, which is typically made of resin such as PVC, becomes less elastic. Consequently, even if the clamping portion is clamped with the clamping member, the flexible tube might not deform satisfactorily and might not be closed. If a clamping device capable of generating a large clamping force is used, a certain level of clamping force can be obtained regardless of the temperature of the flexible tube. In that case, however, a clamping member that consumes high power needs to be used, leading to a problem that the heat generated at the activation may affect the capability of distinguishing bubbles from liquid in the clamping portion.

The present invention has been conceived in view of such circumstances and provides a clamping device that is always capable of clamping a flexible tube in a good manner without a large clamping force and assuredly closing the flexible tube.

According to the teachings herein, there is provided a clamping device including a holding member that holds a flexible tube in which a fluid is allowed to flow, and a clamping member that clamps and closes a clamping portion of the flexible tube that is held by the holding member. The clamping device further includes a heating device that heats the clamping portion of the flexible tube.

According to the teachings herein, the clamping device as taught herein further includes a temperature-detecting device that detects a temperature resulting from the heating by the heating device. The clamping portion of the flexible tube is kept at a predetermined temperature by controlling, in accordance with the temperature detected by the temperature-detecting device, the heating by the heating device.

According to the teachings herein, in the clamping device as taught herein, the holding member includes a body portion that holds the flexible tube and that is provided with the clamping member, a lid portion provided to the body portion and that covers and nips the clamping portion of the flexible tube held by the body portion, and a fitting groove provided in the body portion or the lid portion and in which the flexible tube is fittable in a lengthwise direction. The heating device is provided to the body portion or the lid portion that is provided with the fitting groove.

According to the teachings herein, in the clamping device as taught herein, the flexible tube forms a transfusion line through which liquid is injected into a patient, the holding member is provided with a bubble-detecting device that detects bubbles contained in the liquid flowing in the flexible tube, and the clamping member clamps and closes the clamping portion of the flexible tube under a condition that any bubbles are detected by the bubble-detecting device.

According to the teachings herein, the clamping device includes the heating device that heats the clamping portion of the flexible tube. Hence, the flexible tube can always be clamped in a good manner and can assuredly be closed without a large clamping force.

According to the teachings herein, the clamping device includes the temperature-detecting device that detects the temperature resulting from the heating by the heating device. The clamping portion of the flexible tube is kept at a predetermined temperature by controlling, in accordance with the temperature detected by the temperature-detecting device, the heating by the heating device. Hence, the clamping portion of the flexible tube can be prevented from being heated excessively and becoming unable to fully restore its original shape after being clamped.

According to the teachings herein, the holding member includes the body portion that holds the flexible tube and that is provided with the clamping member, the lid portion provided to the body portion and that covers and nips the clamping portion of the flexible tube held by the body portion, and the fitting groove provided in the body portion or the lid portion and in which the flexible tube is fittable in the lengthwise direction. Furthermore, the heating device is provided to the body portion or the lid portion that is provided with the fitting groove. Hence, the heating of the clamping portion by the heating device can be performed efficiently.

According to the teachings herein, the flexible tube forms the transfusion line through which the liquid is injected into the patient, the holding member is provided with the bubble-detecting device that detects bubbles contained in the liquid flowing in the flexible tube, and the clamping member clamps and closes the clamping portion of the flexible tube under a condition that any bubbles are detected by the bubble-detecting device. Hence, if any bubbles are contained in the liquid injected into the patient, the clamping portion can be closed assuredly and promptly. Thus, such bubbles can more assuredly be prevented from reaching the patient.

DETAILED DESCRIPTION

An embodiment of the present invention will now be described specifically with reference to the drawings.

Figure 1:
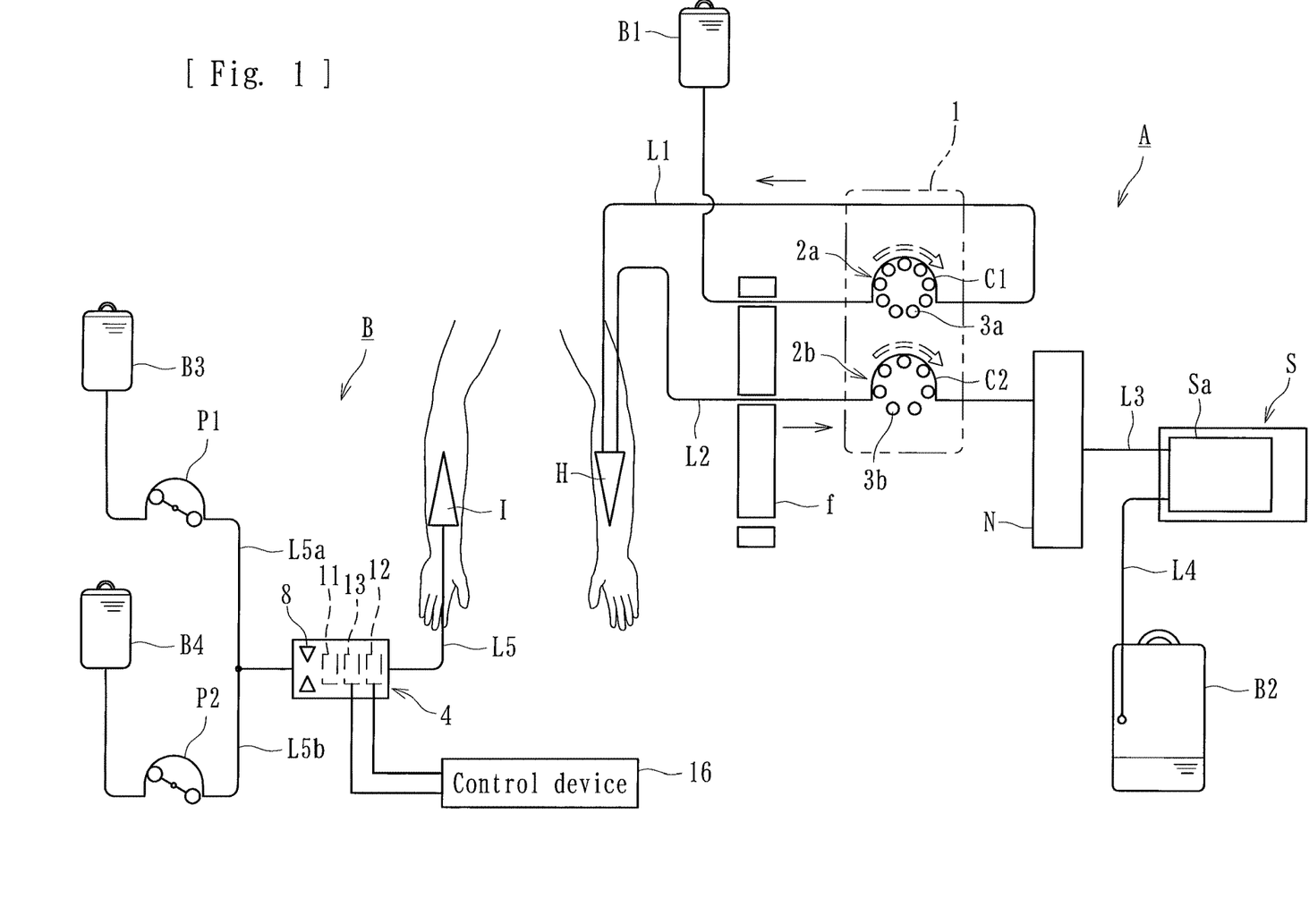
FIG. 1 is a schematic diagram of a blood glucose controlling device to which a clamping device according to an embodiment of the present invention is applied.

A clamping device according to the present embodiment is applied to a blood glucose controlling device as illustrated in FIG. 1. The blood glucose controlling device includes a dilution device A, a blood-sugar-level-measurement device S, and a transfusion device B. The dilution device A dilutes blood of a patient with a predetermined diluent. The diluted blood is sent to the blood-sugar-level-measurement device S through a flow route L3, and the transfusion device B can transfuse the diluted blood into the patient in accordance with the blood sugar level measured by the blood-sugar-level-measurement device S.

The dilution device A according to the present embodiment includes a flow route L1 that is connected at one end thereof to a storage bag B1 that stores the diluent and at the other end thereof to an invasive catheter H. The flow route L1 is connected to a squeezable portion C1 at a halfway position thereof. The dilution device A according to the present embodiment further includes a flow route L2 that is connected at one end thereof to the invasive catheter H and at the other end thereof to a mixing unit N such as a chamber. The flow route L1 and the flow route L2 are each a flexible tube in which liquid is allowed to flow. A liquid-exhaustion detector f is provided over halfway positions of the flow routes L1 and L2, so that liquid exhaustion can be detected.

The invasive catheter H is connected to both the other end of the flow route L1 and the one end of the flow route L2 and is indwelling into the patient. The invasive catheter H collects the blood of the patient while allowing the diluent in the storage bag B1 to be introduced thereinto, thereby being capable of supplying the blood mixed with the diluent to the mixing unit N. The mixing unit N is connected to the blood-sugar-level-measurement device S. The diluted liquid substantially evenly mixed in the mixing unit N is supplied to the blood-sugar-level-measurement device S through the flow route L3.

The squeezable portion C1 of the flexible tube forming the flow route L1 and a squeezable portion C2 of the flexible tube forming the flow route L2 are attached to the peristaltic pump 1 according to the present embodiment. The peristaltic pump 1 is capable of allowing the diluent and the blood to flow simultaneously at a predetermined ratio. The peristaltic pump 1 includes a first rotor 2a, a second rotor 2b, rollers 3a provided to the first rotor 2a, and rollers 3b provided to the second rotor 2b. When a motor, which is not illustrated, is activated, the first rotor 2a and the second rotor 2b are simultaneously rotated. Accordingly, the rollers 3a of the first rotor 2a squeeze the squeezable portion C1, and the rollers 3b of the second rotor 2b squeeze the squeezable portion C2.

The blood-sugar-level-measurement device S includes glucose sensor Sa. The glucose sensor Sa is capable of, for example, decomposing grape sugar while continuously introducing the diluted liquid supplied from the dilution device A onto an enzyme film and thus measuring the blood sugar level from the value of a current generated at the decomposition. The blood-sugar-level-measurement device S is connected to a drainage bag B2 with a flow route L4. Thus, the blood collected from the patient is diluted with the diluent at a predetermined ratio, is subjected to the measurement of the blood sugar level by the glucose sensor Sa of the blood-sugar-level-measurement device S, and is discharged into the drainage bag B2.

If the blood sugar level measured by the blood-sugar-level-measurement device S is too high, the transfusion device B can lower the blood sugar level by injecting insulin into the patient, if the blood sugar level is too low, the transfusion device B can raise the blood sugar level by injecting grape sugar (glucose) into the patient. The transfusion device B includes a storage bag B3 that stores insulin, a storage bag B4 that stores glucose, a transfusion line L5 for injecting liquid into the patient, and a clamping device 4.

The transfusion line L5 is connected to a puncture needle I at one end thereof and to branch lines (L5a and L5b) at the other end thereof. The branch line L5a is connected to the storage bag B3, and the branch line L5b is connected to the storage bag B4. The branch line L5a is provided with a peristaltic pump P1. When the peristaltic pump P1 is activated, the insulin in the storage bag B3 can be made to flow through the transfusion line L5. The branch line L5b is provided with a peristaltic pump P2. When the peristaltic pump P2 is activated, the glucose in the storage bag B4 can be made to flow through the transfusion line L5.

In a state where the puncture needle I is stuck in the patient, if the blood sugar level measured by the blood-sugar-level-measurement device S is too high, the peristaltic pump P1 is activated so that the insulin can be injected into the patient through the puncture needle I. If the blood sugar level measured by the blood-sugar-level-measurement device S is too low, the peristaltic pump P2 is activated so that the glucose can be injected into the patient through the puncture needle I.

Figure 2:
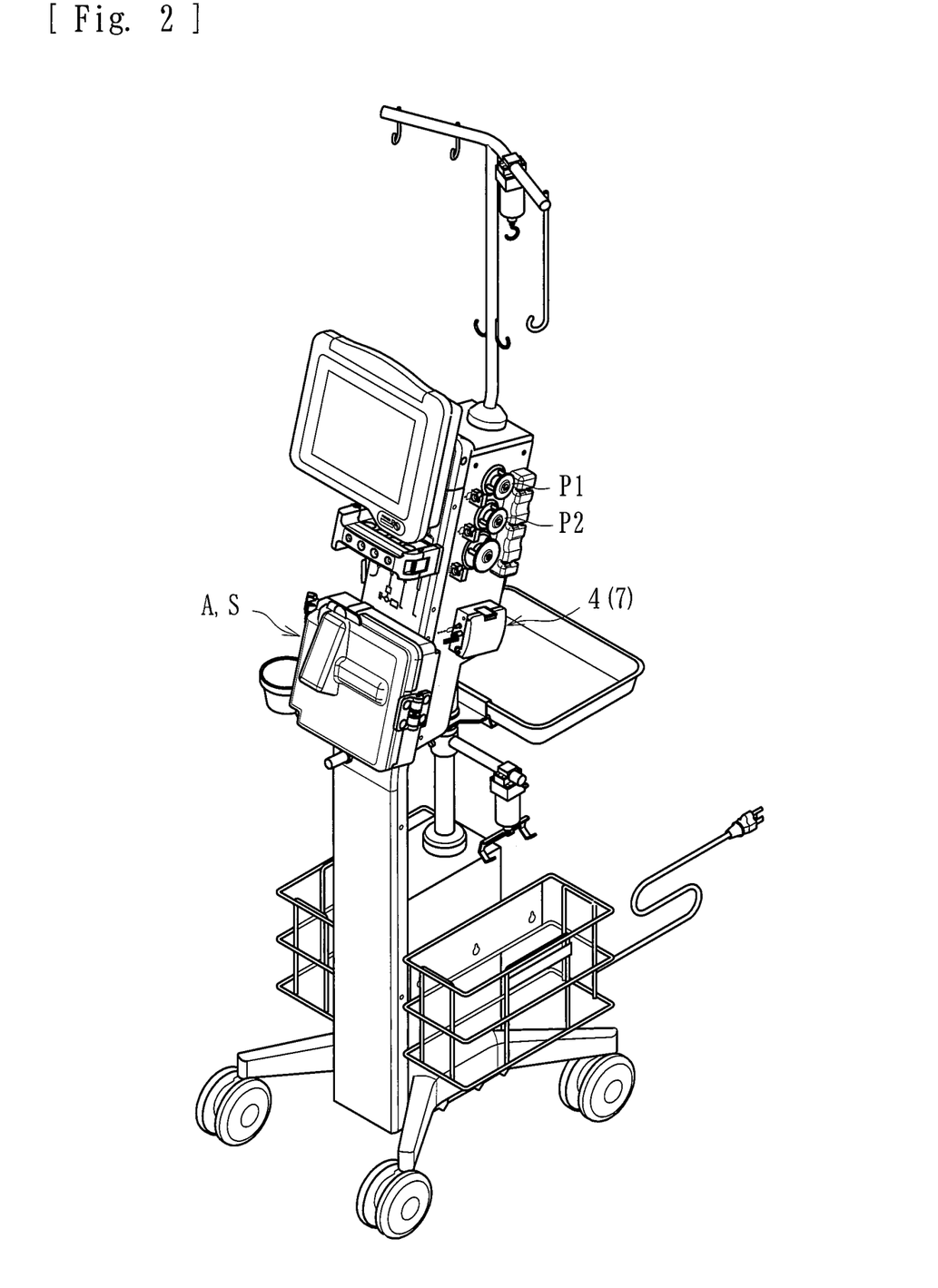
FIG. 2 is an external view of the blood glucose controlling device.
Figure 3:
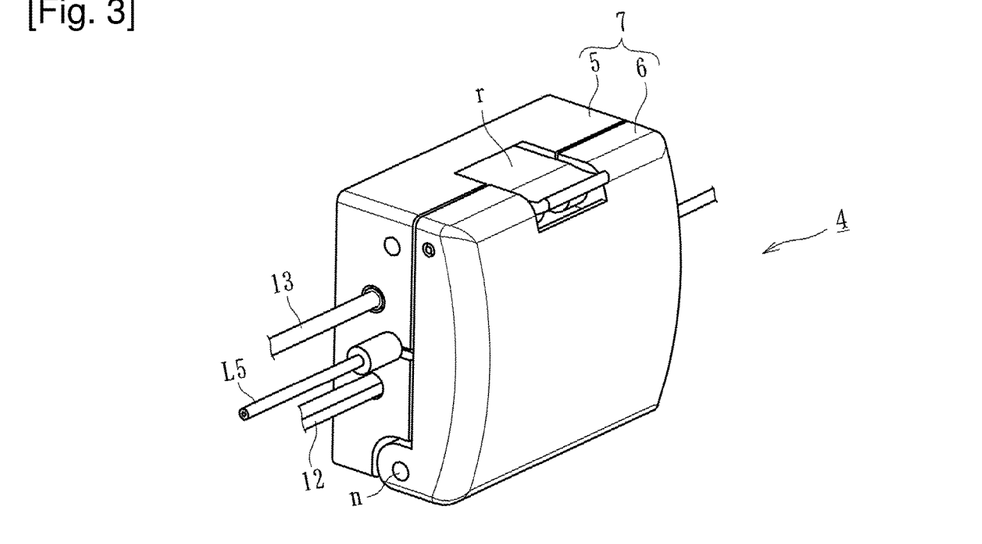
FIG. 3 is a perspective external view of the clamping device (with a lid portion thereof closed) according to the embodiment.
Figure 4:
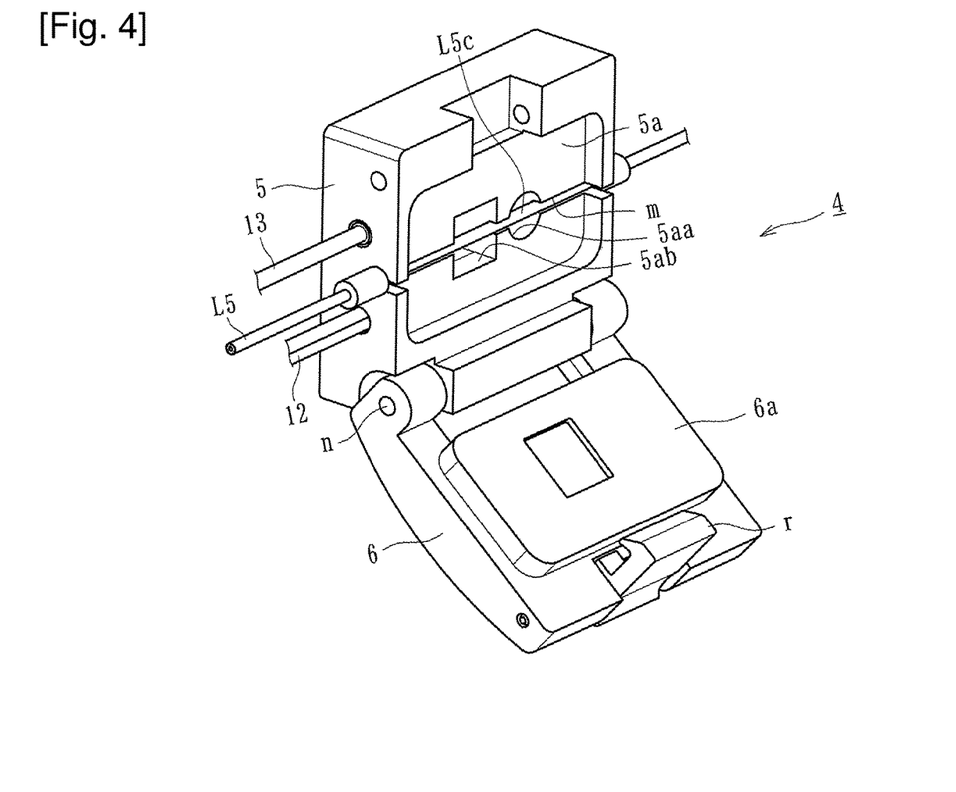
FIG. 4 is another perspective external view of the clamping device (with the lid portion open).
Figure 5:
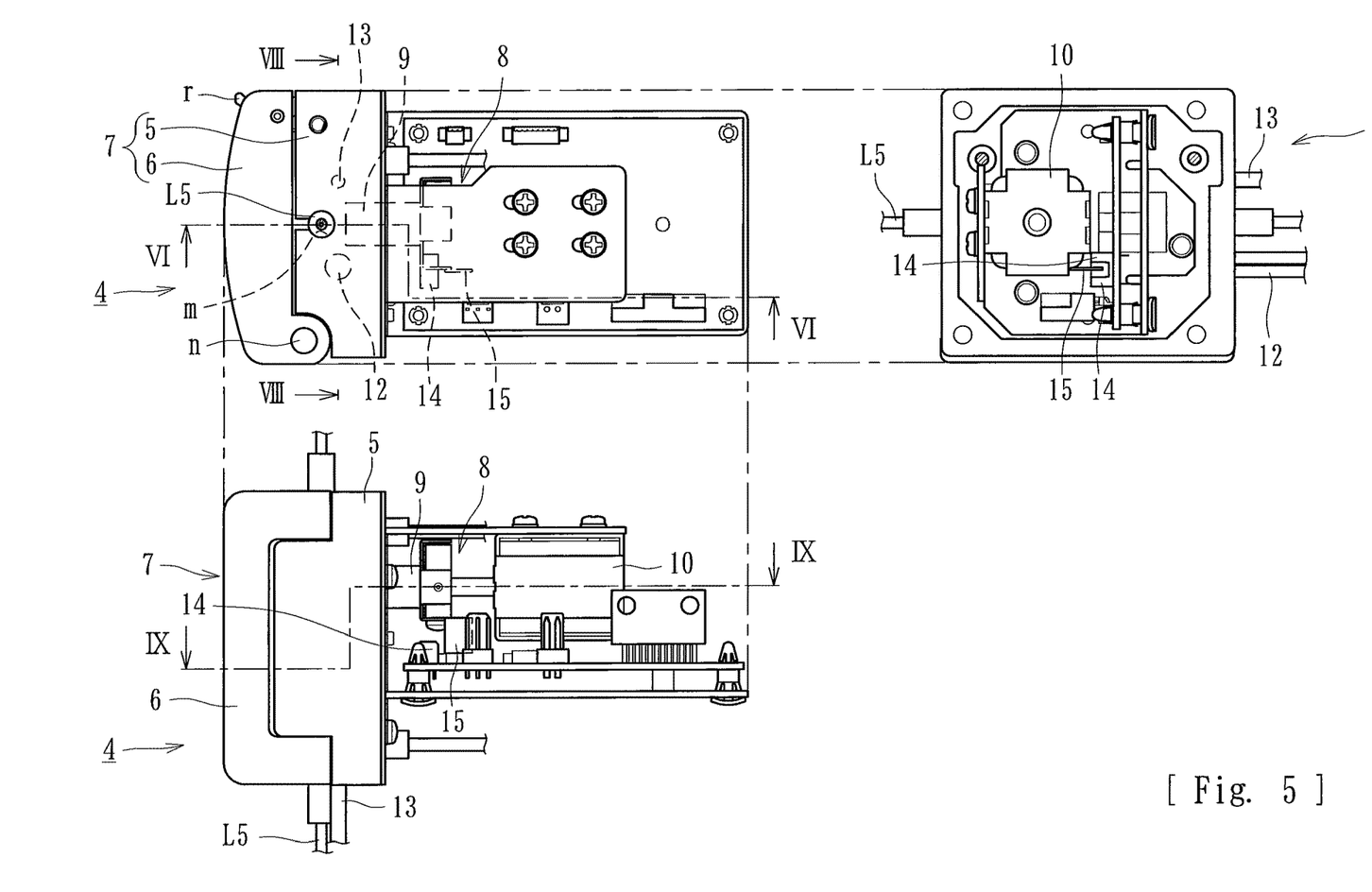
FIG. 5 is a third-angle projection of the clamping device.

As illustrated in FIG. 2, the clamping device 4 according to the present embodiment is attached to a side face of the body of the blood glucose controlling device and includes, as illustrated in FIGS. 1 and 2, a holding member 7 that is capable of holding a flexible tube (in the present embodiment, the flexible tube forming the transfusion line L5) in which a fluid is allowed to flow, a clamping member 8 that is capable of clamping and thus closing a clamping portion of the flexible tube held by the holding member 7 as intended, a bubble-detecting device 11, a heating device 12, and a temperature-detecting device 13. The flexible tube or the like forming the transfusion line L5 is preferably made of PVC (polyvinyl chloride) or the like that is resistant to sterilization.

The holding member 7 forms the housing of the clamping device 4. As illustrated in FIGS. 3 to 7, the holding member 7 includes a body portion 5 that holds the flexible tube (the transfusion line L5) and to which the clamping member 8 is attached, and a lid portion 6 that is attached to the body portion 5 and that can cover and nip a clamping portion L5c of the flexible tube (the transfusion line L5) that is held by the body portion 5. The lid portion 6 is openable and closable by swinging about a swing shaft n, and is lockable when a lock r catches the body portion 5.

The body portion 5 (specifically, a nipping part 5a of the body portion 5) according to the present embodiment has a fitting groove m in which the flexible tube (the transfusion line L5) is fittable in the lengthwise direction thereof. Specifically, the fitting groove m is a U-shaped groove that conforms to the outer peripheral surface of the flexible tube forming the transfusion line L5. A part including the clamping portion L5c is fitted into the fitting groove m, whereby the flexible tube can be positioned and be held therein. The fitting groove m according to the present embodiment is provided in the body portion 5. Alternatively, the fitting groove m may be provided in the lid portion 6 (for example, in a nipping part 6a of the lid portion 6).

When the lid portion 6 is closed, the nipping part 5a of the body portion 5 and the nipping part 6a of the lid portion 6 meet each other, whereby the flexible tube (the transfusion line L5) fitted in the fitting groove m can be nipped therebetween. The nipping part 5a of the body portion 5 is made of a material, such as an aluminum material, having an excellent heat-transmission characteristic and can facilitate the efficient heating of the clamping portion L5c by the heating device 12 to be described below. The other part around the nipping part 5a is made of a heat-insulating material. In the drawings, reference numeral 5aa denotes a through hole in which a rod 9 included in the clamping member 8 is movable back and forth, and reference numeral 5ab denotes a through hole through which an infrared-ray-emitting element 11a and an infrared-ray-receiving element 11b of the bubble-detecting device 11 face each other.

The clamping member 8 is capable of clamping and thus closing, as intended, the clamping portion L5c of the flexible tube (the transfusion line L5) held by the holding member 7 (the body portion 5). The clamping member 8 includes the rod 9 and a solenoid 10. When the solenoid 10 is energized, the rod 9 that has been in an unclamping state (see FIG. 6) moves toward the flexible tube and falls into a clamping state (see FIG. 7). Accordingly, the tip of the rod 9 presses and deforms the clamping portion L5c, whereby the flow route is closed. When the energization of the solenoid 10 is stopped, the rod 9 that has been in the clamping state moves toward the other side and returns to the unclamping state. Accordingly, the clamping portion L5c restores its original shape, and the flow route is opened.

Figure 6:
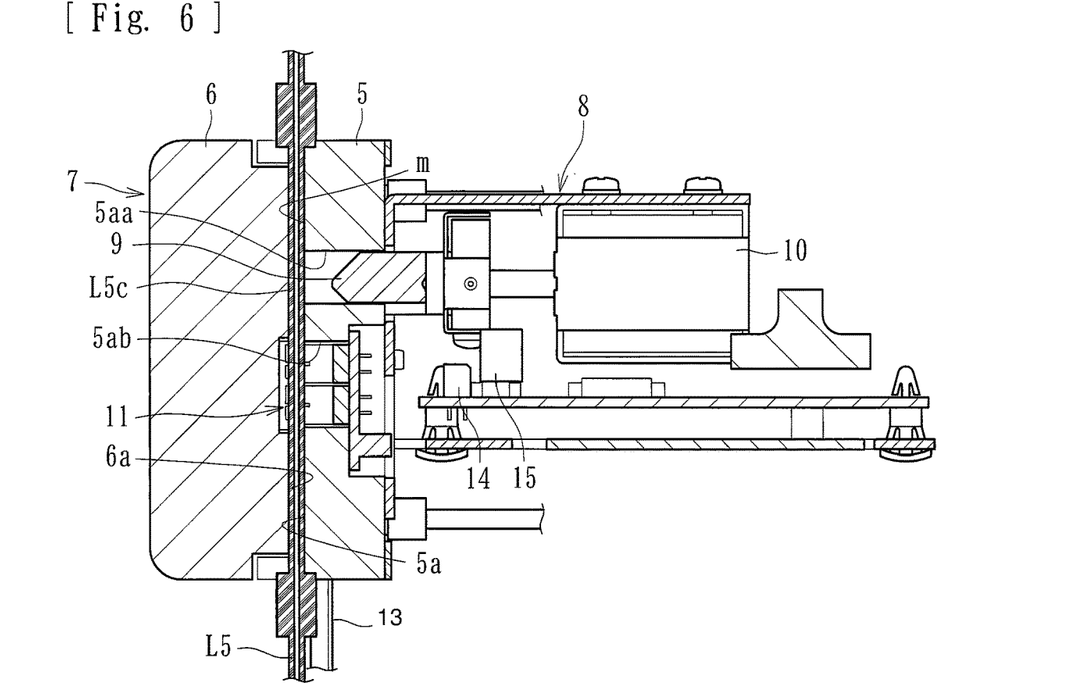
FIG. 6 is a longitudinal sectional view (along line VI-VI illustrated in FIG. 5) of the clamping device (before clamping).
Figure 7:
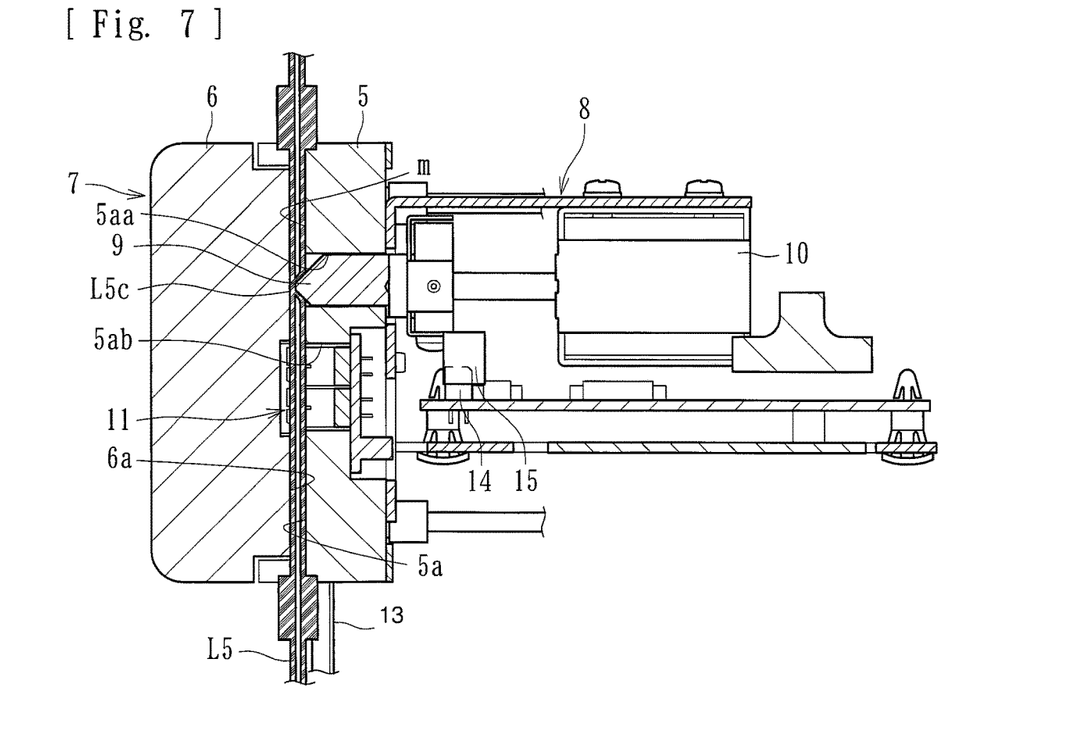
FIG. 7 is another longitudinal sectional view of the clamping device (during clamping).

The clamping member 8 according to the present embodiment includes a light-blocking plate 15 that is movable along with the rod 9, and a photoelectric element 14 including an element on the light-emitting side that emits light and an element on the light-receiving side that receives the light. When the rod 9 is in the unclamping state, the light from the light-emitting side of the photoelectric element 14 can be received by the light-receiving side. When the rod 9 is in the clamping state, the light from the light-emitting side of the photoelectric element 14 is blocked by the light-blocking plate 15. Therefore, if whether or not the light is received by the element on the light-receiving side of the photoelectric element 14 is detected, whether the rod 9 is in the clamping state or in the unclamping state can be identified.

Figure 9:
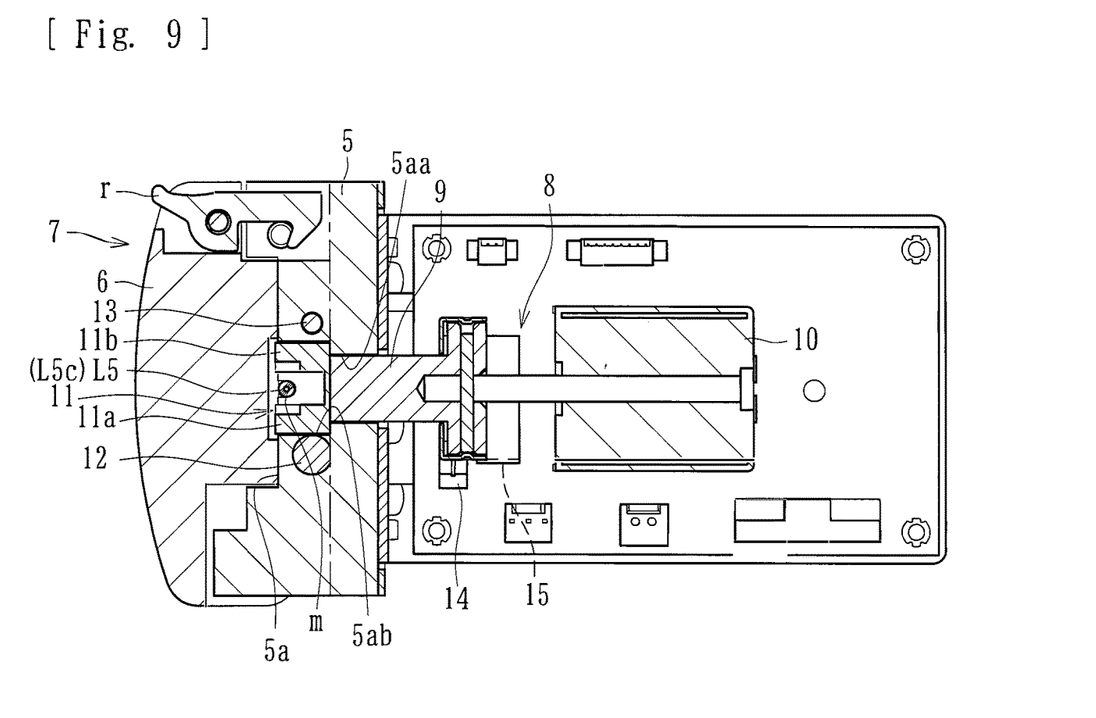
FIG. 9 is a sectional view along line IX-IX illustrated in FIG. 5.

The bubble-detecting device 11 is a sensor that is capable of detecting bubbles (air) in the liquid flowing in the transfusion line L5. As illustrated in FIGS. 6, 7, and 9, the bubble-detecting device 11 includes, for example, the infrared-ray-emitting element 11a formed of a piezoelectric element, and the infrared-ray-receiving element 11b formed of a piezoelectric element. As illustrated in FIG. 9, the infrared-ray-emitting element 11a and the infrared-ray-receiving element 11b are arranged face to face at one edge and the other edge, respectively, of the fitting groove m provided in the body portion 5, so that infrared rays can pass through the flexible tube forming the transfusion line L5 fitted in the fitting groove m.

The infrared-ray-emitting element 11a is capable of applying infrared rays toward the flexible tube forming the transfusion line L5 fitted in the fitting groove m, and the infrared-ray-receiving element 11b is capable of receiving the oscillation. The infrared-ray-receiving element 11b is configured such that the voltage thereof changes in accordance with the quantity of light received. If the detected voltage exceeds a predetermined threshold, it is detected that the liquid (insulin or glucose) flowing in the transfusion line L5 contains bubbles. The quantity of light is smaller in the case of bubbles (because of a lens effect) than in the case of the liquid such as insulin or glucose. Therefore, if the voltage detected by the infrared-ray-receiving element 11b becomes lower than the predetermined threshold, it is regarded that bubbles are detected.

Thus, in the present embodiment, if any bubbles are detected by the bubble-detecting device 11, the clamping member 8 can clamp and close the clamping portion L5c of the flexible tube forming the transfusion line L5. Hence, during a transfusion process in which insulin, glucose, or the like is injected into the patient, bubbles contained in the liquid can be prevented from being injected into the body of the patient.

Figure 8:
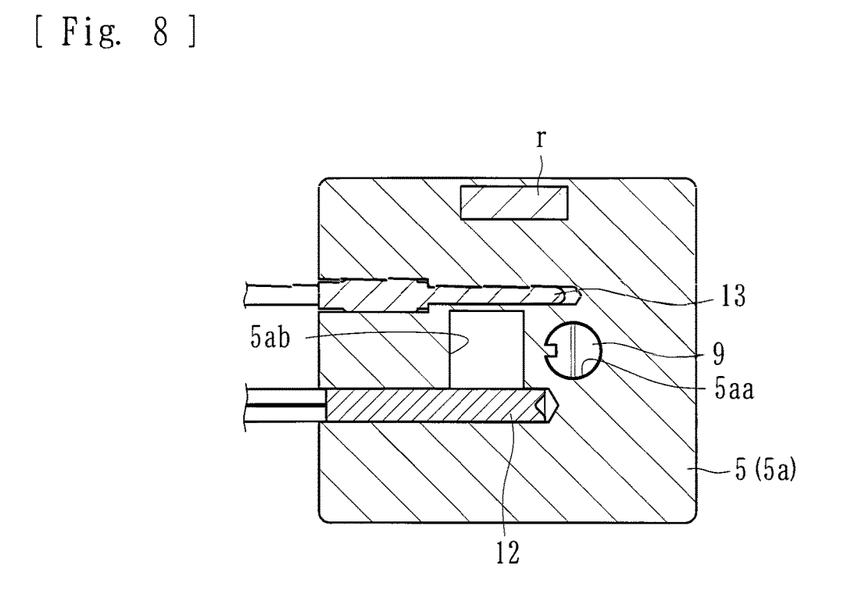
FIG. 8 is a sectional view along line VIII-VIII illustrated in FIG. 5.

The heating device 12 is a heater or the like including a coil that is capable of generating heat when energized or a heating mechanism equivalent thereto. As illustrated in FIG. 8, the heating device 12 is provided in the nipping part 5a of the body portion 5 and is capable of heating the clamping portion L5c of the flexible tube. That is, when the heating device 12 is energized and generates heat, the heat is transmitted through the nipping part 5a that is made of an aluminum material and can heat the clamping portion L5c of the flexible tube fitted in the fitting groove m.

The temperature-detecting device 13 is a sensor that is capable of detecting the temperature resulting from the heating by the heating device 12 (in the present embodiment, the temperature of the nipping part 5a). As illustrated in FIG. 1, the temperature-detecting device 13 is connected to a control device 16. The control device 16 is a microcomputer or the like that is connected to the heating device 12 and to the temperature-detecting device 13. The control device 16 is capable of controlling the heating by the heating device 12 in accordance with the temperature detected by the temperature-detecting device 13. Under such control, the clamping portion L5c of the flexible tube can be kept at a predetermined temperature (for example, a temperature+/−1° C. of a target temperature).

The present embodiment employs the heating device 12 that is capable of heating the clamping portion L5c of the flexible tube forming the transfusion line L5. Hence, the flexible tube can always be clamped in a good manner and can assuredly be closed without a large clamping force. That is, since the clamping portion L5c is heated, the temperature dependency of the flexible tube (particularly, PVC) with respect to the flexibility can be eliminated. Hence, the clamping portion L5c can always be clamped in a good manner.

The present embodiment further employs the temperature-detecting device 13 that is capable of detecting the temperature resulting from the heating by the heating device 12. Since the heating by the heating device 12 is controlled in accordance with the temperature detected by the temperature-detecting device 13, the clamping portion L5c of the flexible tube can be kept at a predetermined temperature. Hence, the clamping portion L5c of the flexible tube can be prevented from being heated excessively and becoming unable to fully restore its original shape after being clamped.

The holding member 7 includes the body portion 5 that holds the flexible tube and that is provided with the clamping member 8, the lid portion 6 provided to the body portion 5 and that is capable of covering and nipping the clamping portion L5c of the flexible tube held by the body portion 5, and the fitting groove m provided in the body portion 5 and in which the flexible tube is fittable in the lengthwise direction. Furthermore, the heating device 12 is attached to the body portion 5, in which the fitting groove m is provided. Hence, the heating of the clamping portion L5c by the heating device 12 can be performed efficiently. Note that the fitting groove m may be provided in the lid portion 6 (for example, the nipping part 6a of the lid portion 6). In that case, the heating device 12 and the temperature-detecting device 13 are preferably attached to the lid portion 6 provided with the fitting groove m.

The flexible tube forms the transfusion line L5 through which liquid is injected into the patient. On the other hand, the holding member 7 includes the bubble-detecting device 11 that is capable of detecting bubbles contained in the liquid flowing in the flexible tube. Furthermore, if any bubbles are detected by the bubble-detecting device 11, the clamping member 8 can clamp and close the clamping portion L5c of the flexible tube. Hence, if any bubbles are contained in the liquid injected into the patient, the clamping portion L5c can be closed assuredly and promptly. Thus, such bubbles can more assuredly be prevented from reaching the patient.

While an embodiment has been described above, the present invention is not limited thereto. For example, the heating device 12 as a heater may be replaced with a heating device including a fan that blows warm air, a Peltier element, or the like. Alternatively, the body portion 5 may be made of a material having a low heat-transmission characteristic but may include a member having a high heat-transmission characteristic and the heating device 12 in the body portion 5. As another alternative, the clamping portion L5c may be heated only with the heating device 12 without providing the temperature-detecting device 13, or the flexible tube may be clamped simply without providing the bubble-detecting device 11. Moreover, while the above embodiment is applied to the transfusion device 8 included in a blood glucose controlling device, the present invention may be applied to a device that is provided to an extracorporeal circulation circuit such as a blood circuit included in a blood purification apparatus used in dialysis treatment or the like. In addition, the bubble-detecting device 11 is not limited to a device based on infrared rays as in the above embodiment and may be based on ultrasonic waves.

The present invention is also applicable to another device having any other external shape or any other additional functions, as long as the clamping device includes a heating device that is capable of heating a clamping portion of a flexible tube.

REFERENCE SIGNS LIST 1 peristaltic pump
2a first rotor
2b second rotor
3a, 3b roller
4 clamping device
5 body portion
6 lid portion
7 holding member
8 clamping member
9 rod
10 solenoid
11 bubble-detecting device
12 heating device
13 temperature-detecting device
14 photoelectric element
15 light-blocking plate
16 control device
A dilution device
S blood-sugar-level-measurement device
B transfusion device
L5 transfusion line
L5c clamping portion

The invention claimed is:

1. A clamping device comprising:
a holding member that includes a nipping part and a fitting groove, where the fitting groove is formed in the holding member and holds a flexible tube in which a fluid is allowed to flow by the nipping part and the nipping part nips the flexible tube in a state where the flexible tube is fitted in the fitting groove; and
a clamping member that clamps and closes a clamping portion of the flexible tube that is held by the holding member,
wherein the clamping device further includes a heating device that heats the clamping portion of the flexible tube that is nipped by the nipping part in a state where the flexible tube is fitted in the fitting groove via the nipping part, and
wherein the holding member is provided with the heating device and the clamping member; the holding member includes a through hole that houses a portion of the clamping member and the clamping member is movable in and out of the holding member via the through hole; and the holding member comprises a temperature-detecting device that is spaced apart from the heating device by the through hole.

2. The clamping device according to claim 1, wherein the temperature detecting device detects a temperature resulting from the heating by the heating device,
wherein the clamping portion of the flexible tube is kept at a predetermined temperature by controlling, in accordance with the temperature detected by the temperature-detecting device, the heating by the heating device.

3. The clamping device according to claim 1, wherein the holding member includes:
a body portion that holds the flexible tube and that is provided with the clamping member;
a lid portion comprising the nipping part or the fitting groove, the lid portion provided to the body portion and that covers and nips the clamping portion of the flexible tube held by the body portion; and the fitting groove provided in the body portion if the lid portion comprises the nipping part or the fitting groove is provided in the lid portion when the body portion comprises the nipping part and in which the flexible tube is fittable in a lengthwise direction, and wherein the heating device is provided to the body portion or the lid portion that is provided with the fitting groove.

4. The clamping device according to claim 1, wherein the flexible tube forms a transfusion line through which liquid is injected into a patient, the holding member is provided with a bubble-detecting device that detects bubbles contained in the liquid flowing in the flexible tube, and the clamping member clamps and closes the clamping portion of the flexible tube under a condition that any bubbles are detected by the bubble-detecting device.

5. The clamping device according to claim 2 wherein the flexible tube forms a transfusion line through which liquid is injected into a patient, the holding member is provided with a bubble-detecting device that detects bubbles contained in the liquid flowing in the flexible tube, and the clamping member clamps and closes the clamping portion of the flexible tube under a condition that any bubbles are detected by the bubble-detecting device.

6. The clamping device according to claim 3, wherein the flexible tube forms a transfusion line through which liquid is injected into a patient, the holding member is provided with a bubble-detecting device that detects bubbles contained in the liquid flowing in the flexible tube, and the clamping member clamps and closes the clamping portion of the flexible tube under a condition that any bubbles are detected by the bubble-detecting device.

7. The clamping device according to claim 1, comprising a second through hole located adjacent to the through hole, the second through hole includes an infrared-ray-emitting element.

8. The clamping device according to claim 7, wherein the holding member includes an infrared-ray-receiving element facing the infrared-ray-emitting element.

9. The clamping device according to claim 1, wherein the clamping member includes a rod and a solenoid, and the solenoid, when energized, moves the rod between a clamping state and an unclamping state.

10. The clamping device according to claim 9, wherein the clamping member includes a light-blocking plate that is movable along with the rod.

11. The clamping device according to claim 10, wherein the light-blocking plate blocks a photoelectric element that emits light when the clamping member is in the clamping state.

12. The clamping device according to claim 9, wherein the clamping member includes a photoelectric element that emits light and an element that receives the light.

13. The clamping device according to claim 1, wherein the heating device includes a coil that is capable of generating heat when energized.

14. The clamping device according to claim 1, wherein the heating device extends into the nipping part of the holding member and the heating device transmits heat into the nipping part when the heating device is energized and the nipping part is made of aluminum.

15. The clamping device according to claim 1, comprising a second through hole, wherein the second through hole contains an infrared-ray-receiving element or a rod.

16. The clamping device according to claim 1, wherein the heating device includes a fan that blows warm air, or a Peltier element.

17. A medical apparatus comprising the clamping device of claim 1, wherein the medical apparatus is part of a transfusion device included in a blood glucose controlling device or part of an extracorporeal circulation circuit that provides dialysis treatment.

\* \* \* \* \*